United States Patent [19]
Takeuchi et al.

[11] Patent Number: 5,215,981
[45] Date of Patent: Jun. 1, 1993

[54] POLYETHER ANTIBIOTIC MI215-NF3 SUBSTANCE, PRODUCTION PROCESS THEREOF, AND AGENT FOR CONTROL OF CHICKEN COCCIDIOSIS

[75] Inventors: Tomio Takeuchi, Tokyo; Yoshikazu Takahashi, Tama; Masa Hamada, Naito; Hiroshi Naganawa, Tokyo; Kiyoshi Sato, Hatano, all of Japan

[73] Assignees: Hokko Chemical Industry Co., Ltd.; Zaidan Hojin Biseibutsu Kagaku Kenkyu Kai, both of Tokyo, Japan

[21] Appl. No.: 720,758
[22] PCT Filed: Dec. 28, 1989
[86] PCT No.: PCT/JP89/01328
§ 371 Date: Jul. 1, 1991
§ 102(e) Date: Jul. 1, 1991
[87] PCT Pub. No.: WO90/07510
PCT Pub. Date: Jul. 12, 1990

[30] Foreign Application Priority Data

Dec. 29, 1988 [JP] Japan ................... 63-335330

[51] Int. Cl.$^5$ .................. A61K 31/555; C07D 309/02
[52] U.S. Cl. ................... 514/184; 514/191; 514/460; 514/459; 549/211; 549/343
[58] Field of Search .......... 549/343, 211; 514/460, 514/184, 191, 459

[56] References Cited

U.S. PATENT DOCUMENTS 4,582,822 4/1986 Hamill et al. .......... 514/25
4,683,201 7/1987 Hamill et al. .......... 435/75

FOREIGN PATENT DOCUMENTS 61-191190 5/1986 Japan.
62-00934 5/1987 Japan.
63-218679 9/1988 Japan.

Primary Examiner—C. Warren Ivy
Attorney, Agent, or Firm—Lalos & Keegan

[57] ABSTRACT

In this invention, a new microbial strain which is a strain of Actinomycetes and belongs to the genus Actinomadura, namely Actinomadura sp. MI215-NF3 strain is cultured, and MI215-NF3 substance, a novel antibiotic classifiable as a polyether antibiotic, is recovered from the resultant culture. MI215-NF3 substance and its salts obtained according to this invention are useful for therapeutic treatment of chicken coccidiosis and also have useful antibacterial activities against certain species of bacteria.

2 Claims, 2 Drawing Sheets

POLYETHER ANTIBIOTIC MI215-NF3 SUBSTANCE, PRODUCTION PROCESS THEREOF, AND AGENT FOR CONTROL OF CHICKEN COCCIDIOSIS

TECHNICAL FIELD

This invention relates to a novel antibiotic substance MI215-NF3 and salts thereof and also relates to a process for production of the MI215-NF3 substance or salts thereof. This invention further relates to agent for control of chicken coccidiosis, which contains the MI215-NF3 substance or a salt thereof as an active ingredient. Furthermore, the present invention also pertains to a new microorganism, Actinomadura sp. MI215-NF3 strain which has characteristic capable of producing MI215-NF3 substance.

PRIOR ART

Various antibiotics of polyether type are known to have antibacterial activities. Monensin (see Japanese Patent Publication No. 113/70) and salinomycin (see "The Journal of Antibiotics", 27, 814–821), which belong to the polyether antibiotics, are used as agents for control of chicken coccidiosis.

Coccidiosis provides a serious problem in the poultry farming. There has hence been a continued desire for the discovery or development of a new compound which can exhibit superior anticoccidial activity and properties to the compounds previously known or used to date. Investigations are now made to achieve this end.

DISCLOSURE OF THE INVENTION

With a view toward discovering useful novel antibiotics, we, the present inventors, have therefore proceeded with investigations. As a result, we have succeeded in isolating a new strain belonging to the genus Actinomadura. We have also found that this new strain can produce a novel polyether antibiotic. This antibiotic is now named MI215-NF3 substance. Further, it has also been uncovered that this MI215-NF3 substance and its salts (carboxylates) exhibit an activity to control chicken coccidiosis. The present inventors have proceeded with the investigation further, to determine the chemical structure of MI215-NF3 substance, whereby MI215-NF3 substance has been confirmed to be a novel compound. In addition, it has also been found that MI215-NF3 substance can be represented by the following formula (I):

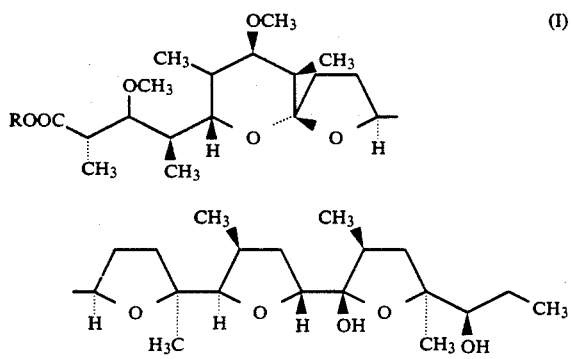

wherein R is a hydrogen atom.

Accordingly, this invention provides the substance which is obtained by culturing a microorganism belonging to the genus Actinomadura and which has been named as MI215-NF3 substance by the present inventors, as well as salts thereof. This invention also provides a process for production thereof, and their use as an agent for control of chicken coccidioses.

In a first aspect of the present invention, therefore, there are provided MI215-NF3 substance having the above formula (I) and a salt thereof.

Although MI215-NF3 substance of the formula (I) is in the form of a free carboxylic acid where R is a hydrogen atom in the formula (I), R in the formula (I) generally can be a metal or ammonium group. Therefore, the present invention also embraces salts of MI215-NF3 substance therein. These salts can be in the form of an alkali metal salt where R is an alkali metal atom in the formula (I), for example, sodium salt, potassium salt and lithium salt, or in the form of an alkaline earth metal salt where R is an alkaline earth metal atom in the formula (I), for example, calcium salt and magnesium salt. They can also be salts of other metals, for example, aluminum salt and iron salt. The ammonium salt can also be included.

Physicochemical properties of MI215-NF3 substance according to the present invention are as follows.

The physicochemical properties of the sodium salt of MI215-NF3 substance will be described hereinafter.

(1) Appearance
Colorless plate crystals.

(2) Elemental analysis

|   | Found | Calculated (for $C_{37}H_{63}O_{11}Na$) |
|---|---|---|
| C | 62.47% | 62.87% |
| H | 8.96% | 8.98% |
| O | 24.60% | 24.90% |
| Na | 3.53% | 3.25% |

(3) Mass spectrometry (SIMS)
m/z 707(M+Na)

(4) Melting point
217–218° C.

(5) Specific optical rotation $[\alpha]^{25}_D = +30.6°$ (c1.0, chloroform)

(6) Infrared absorption specturm (KBr pellet method)
As be shown in FIG. 1 of the accompanying drawings.

(7) Proton nuclear magnetic resonance spectrum
A proton NMR spectrum as measured in deutero-chloroform at 400 MHz and room temperature is as shown in FIG. 2 of the accompanying drawings.

(8) Solubility
Soluble in benzene, chloroform, acetone, ethyl acetate, ethanol and methanol, but insoluble in water.

BRIEF DESCRIPTION OF THE ACCOMPANYING DRAWINGS

Figure 1:
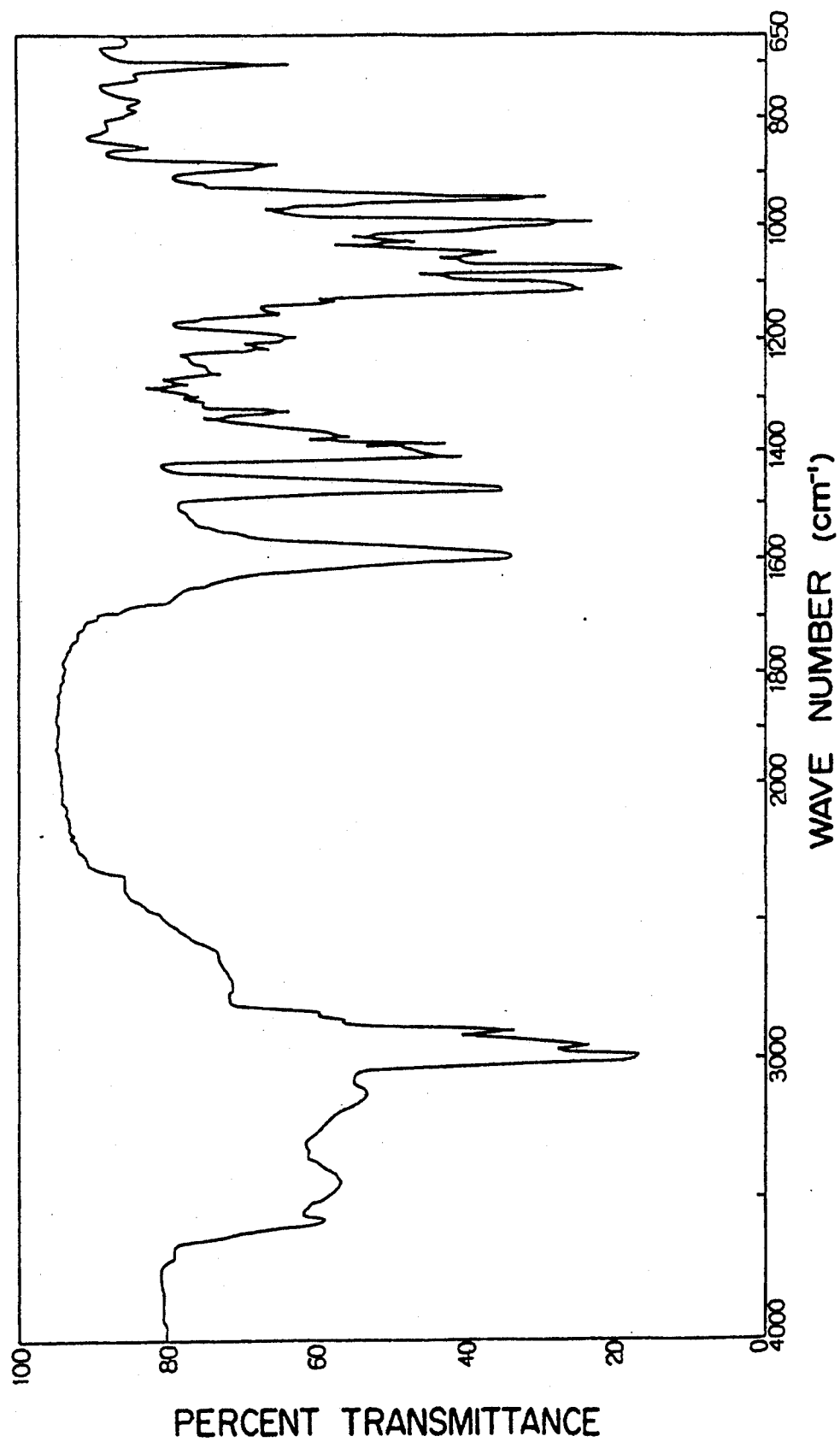
FIG. 1 is an infrared absorption spectrum of the sodium salt of MI215-NF3 substance as measured in accordance with the KBr pellet method.
Figure 2:
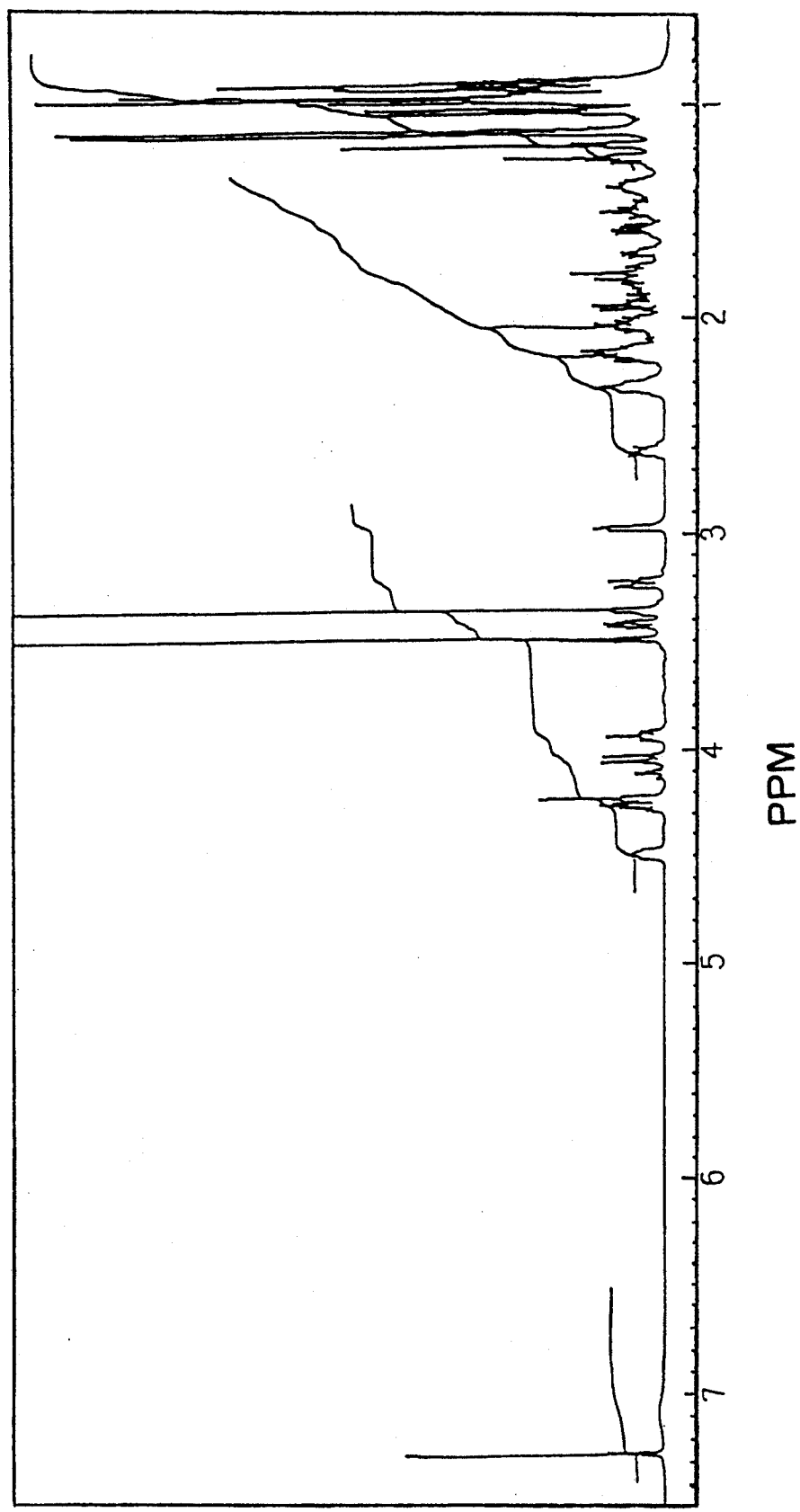
FIG. 2 is a proton nuclear magnetic resonance spectrum of the sodium salt of MI215-NF3 substance as measured in deutero-chloroform at 400 MHz and room temperature.

Biological properties of MI215-NF3 substance according to the present invention are as follows.

The biological properties of the sodium salt of MI215-NF3 substance will be described hereinafter.

(1) Antibacterial spectrum

The antibacterial spectrum of the sodium salt of MI215-NF3 substance against various microorganisms was measured on an agar medium in a manner known per se in the art, using the serial dilution method. The results obtained are summarized in Table 1.

TABLE 1

| Microorganism tested | Minimum inhibitory concentration (MIC) ($\mu$g/ml) |
|---|---|
| Staphylococcus aureus FDA 209P | <0.78 |
| Staphylococcus aureus Smith | 1.56 |
| Micrococcus luteus FDA 16 | 1.56 |
| Micrococcus luteus IFO 3333 | 3.12 |
| Micrococcus luteus PCI 1001 | <0.78 |
| Bacillus anthracis | 0.78 |
| Bacillus subtilis NRRL B-558 | 1.56 |
| Bacillus subtilis PCI 219 | 1.56 |
| Bacillus cereus ATCC 10702 | <0.78 |
| Corynebacterium bovis 1810 | <0.78 |
| Escherichia coli NIHJ | >100 |
| Escherichia coli K-12 | >100 |
| Escherichia coli K-12 ML 1629 | >100 |
| Shigella dysenteriae JS 11910 | 25 |
| Salmonella typhi T-63 | >100 |
| Proteus vulgaris OX 19 | >100 |
| Serratia marcescens | 100 |
| Pseudomonas aeruginosa A3 | >50 |
| Klebsiella pneumoniae PCI 602 | 100 |
| Micobacterium smegmatis ATCC 607 | 12.5 |
| Staphylococcus aureus MS 8710 | 1.56 |
| Staphylococcus aureus MS 9610 | <0.78 |
| Escherichia coli BE 1121 | 3.12 |
| Escherichia coli BE 1186 | 3.12 |
| Escherichia coli BEM 11 | <100 |

(2) Toxicity

When acute toxicity of sodium salt of MI215-NF3 substance was estimated using mice, the MI215-NF3 substance was suspended in physiological saline containing 10% of dimethylsulfoxide. The suspension was injected intraperitoneally, and the mice were observed for 14 days. As a result, the $LD_{50}$ value of the MI215-NF3 substance was then estimated to be 56 mg/kg.

(3) Anticoccidial activity

The activity of MI215-NF3 substance for controlling chicken coccidiosis was tested as summarized below.

1. Newly-hatched chicken (male) were preliminarily raised for 1 week, and two-week-aged chicken were used in the test.
2. The body weights of the chicken were individually measured at the beginning of the test. To make up each test group, ten chicken were selected and alloted in each group so as to minimize variations among the test groups.
3. Chicken were orally inoculated with $5 \times 10^4$ oocysts of *Eimeria tenella* per chick through a stomach probe tube.
4. After the oocyst inoculation, each chick was allowed to take ad libitum a feed which had been prepared by mixing a predetermined amount of MI215-NF3 substance (sodium salt) with a special feed containing no anticoccidial agent. Incidentally, the chicken were also allowed to drink water ad libitum.
5. Up to the 7th day after the oocyst inoculation, the number of oocysts in feces from each chick and the state of the feces were observed everyday.
6. Each chick was anatomized on the 7th day after the infection. Anatomical procedures were as follows.
   1) The body weight of each chick was measured.
   2) Each chick was sacrificed by dislocation of neck cervical fracture.
   3) Each chick was subjected to celiotomy and the cecum was enucleated. The cecum was visually inspected for any lesions on both outer and inner walls of cecum.
   4) The cecum thus inspected was individually disintegrated in a homogenizer, whereby a cecum suspension was prepared. The number of oocysts in the suspension was counted.
   5) Based on the results of the above inspections, the value of ACI (Anticoccidial Index) was determined in accordance with the evaluation method proposed by Merck & Co., Inc., U.S.A., namely, by the following equation:

ACI = (rate (%) of relative body weight gain + survival rate (%) of chick) − (lesion scores + oocyst scores)

Upon determination of the above ACI value, the "rate of weight gain" of the chicken in each group of chicken during the test period for estimation of the drug efficacy and the "rate of relative body weight gain" used for the calculation of ACI were evaluated in accordance with the following equations:

Rate (%) of body weight gain = [(mean body weight of chicken at the end of the test − mean body weight of the chicken at the beginning of the test) ÷ mean body weight of the chicken at the beginning of the test] × 100.
Rate (%) of relative body weight gain = [(rate of body weight gain of the treated group or an infected but non-treated group) ÷ rate of body weight gain of a non-infected and non-treated group] × 100.

On the other hand, the term "lesion scores" means a value which is obtained by evaluating, in terms of indexes, the results of visual inspection of lesions on an enucleated cecum sample. The term "oocyst scores" means a value which is obtained by evaluating, in terms of indexes, the number of oocysts actually counted. Details of the procedure for the determination of ACI values are described, for example, in the literature compiled by Kiyoshi Tsunoda, "Chicken Coccidiosis", pp 95–101, Chikusan Shuppan Sha (May, 1983).

The results obtained are summarized in Table 2.

TABLE 2

| Test Plots Test groups | Test results | | | | | |
|---|---|---|---|---|---|---|
| | Dosage (ppm) | Rate (%) of relative body weight gain | Survival rate (%) | Lesion scores | Oocyst scores | ACI |
| 1. Non-infected control group | 0 | 100 | 100 | 0 | 0 | (200) |
| 2. Group treated with Na salt of MI215-NF3 | 80 | 88.67 | 100 | 4 | 10 | 174.7 |

TABLE 2-continued

| Test Plots Test groups | Test results | | | | | |
|---|---|---|---|---|---|---|
| | Dosage (ppm) | Rate (%) of relative body weight gain | Survival rate (%) | Lesion scores | Oocyst scores | ACI |
| 3. Group treated with Na salt of MI215-NF3 | 100 | 99.39 | 100 | 10.0 | 1 | 188.4 |
| 4. Group treated with Ca salt of MI215-NF3 | 80 | 90.20 | 100 | 2 | 5 | 183.2 |
| 5. Group treated with Al salt of MI215-NF3 | 80 | 90.16 | 100 | 0 | 1 | 189.2 |
| 6. Group treated with Monensin | 100 | 96.13 | 100 | 32.0 | 20 | 144.1 |
| 7. Group treated with Salinomycin | 50 | 71.13 | 100 | 34.0 | 10 | 127.1 |
| 8. Infected control group | 0 | 89.63 | 100 | 40.0 | 30 | 119.6 |

As is apparent from the foregoing results, MI215-NF3 substance and its salts are practically utilizable as an agent for controlling or therapeutically treating chicken or fowl coccidiosis.

Further, in a second aspect of the present invention, there is also provided a process for the production of the antibiotic, MI215-NF3 substance or a salt thereof, characterized in that the process comprises culturing a microorganism, which belongs to the genus Actinomadura and can produce MI215-NF3 substance of the formula (I), and recovering MI215-NF3 substance or a salt thereof from the culture of the microorganism.

Microbiological properties of the MI215-NF3-substance-producing microorganism useful in the process of the present invention are as follows:

Any MI215-NF3-substance-producing microorganism can be used in the present invention irrespective of its species, as far as it has the capability to produce said antibiotic having the physicochemical properties and biological properties described above. The MI215-NF3-substance-producing microorganism to be used in this invention can therefore be selected from a wide variety of microorganisms. Among such microorganisms, one specific preferred example of the MI215-NF3-substance-producing microorganisms is a strain of Actinomycetes to which the strain designation, MI215-NF3, has been allotted and which was isolated by the present inventors from a soil sample collected in Bunkyo-ku, Tokyo.

The microbiological characteristics of MI215-NF3 strain are described below.

1. Morphology

In microscopic observations, aerial hyphae extend from branched substrate mycelia. Substrate mycelia do not split. Spore chains are formed on aerial hyphae and are of a hooked or spiral shape. Matured spore chains generally consist of 7–15 spores. Spores are of an ovoidal shape (with about 0.7×1.0–1.2 micrometers in sizes), and the surface of spore is warty. Neither whirls nor sporangia are observed.

2. Conditions of Growth on Various Media

The standards given in the brackets [] for the corresponding descriptions of colors are same as those given the "Color Harmony Manual" of Container Corporation of America.

(1) Sucrose-nitrate-agar medium (cultured at 30° C.)

On the growth of a colorless to pale orange color [3gc, Lt Tan], white colored aerial hyphae are formed thinly. No soluble pigment is observed.

(2) Glucose-asparagin medium (cultured at 30° C.)

On the growth of a pale yellow brown color [3ic, Lt Amber to 3le, Cinnamon] to light brown color [4ng, Lt Brown], white colored aerial hyphae are formal only in a small quantity. Soluble pigment is produced with a somewhat yellowish tinge.

(3) Glycerin-asparagin-agar medium (ISP-Medium 5, cultured at 30° C.)

On the growth of a pale yellow to pale yellow brown color [2le, Mustard to 3le, Cinnamon], aerial hyphae of white to gray white[2dc Natural] color are formed thinly. Soluble pigment exhibits a slight yellow brown tinge from about the 21st day of incubation.

(4) Starch-inorganic salts-agar medium (ISP-Medium 4, cultured at 30° C.).

On the growth of a pale yellow to pale yellow brown [3ng, Yellow Maple] to yellow brown [3pi, Golden Brown]color, aerial hyphae of pink white [5ba Shell Pink] to gray white [2dc, Natural] color are formed. Soluble pigment is produced with a slight yellow tinge.

(5) Tyrosin-agar medium (ISP-Medium 7, cultured at 30° C.)

On the growth of a pale yellow to yellow brown [3ng, Yellow Maple] to grayish yellow to yellow [3ni, Clove Brown] color, aerial hyphae of yellowish gray [1dc, Putty-lec, Lt Citron Gray] color are formed. Soluble pigment is produced with a slight yellow tinge.

(6) Nutrient-agar medium (cultured at 30° C.)

On the growth of a pale yellow brown [3ic, Lt amber]to grayish yellow brown [3ni, Clove Brown]color, white colored aerial hyphae are formed partly. Soluble pigment is produced with an extremely slight yellow tinge.

(7) Yeast-malt-agar medium (ISP-Medium 2, cultured at 30° C.).

On the growth of a pale yellow brown [2le, Mustard] to grayish yellow brown [2nl, Covert Brown], white to brown white colored aerial hyphae are formed. Soluble pigment is produced with an extremely slight yellow tinge.

(8) Oatmeal-agar medium (ISP-Medium 3, cultured at 30° C.)

On the growth of a pale orange to pale brown [4le, Maple] to yellow brown [3ng, Yellow Maple] color, aerial hyphae of white to pink white [5ba, Shell pink -7ba, Pink Tint] color are formed. Soluble pigment is produced with a slight yellow tinge.

(9) Glycerin-nitrate-agar medium (cultured at 30° C. )

On the growth of a colorless to pale yellow to pale yellow brown [31e, Cinnamon] color, aerial hyphae of white to pink white [5ba, Shell Pink] color are formed. Soluble pigment is produced with a slight yellow tinge.

(10) Starch-agar medium (cultured at 30° C.)

On the growth of a pale yellow brown [21e, Mustard] to grayish yellow brown [3ni, Clove Brown] color, white colored aerial hyphae are formed in a small quantity. No soluble pigment is observed.

(11) Calcium malate-agar medium (cultured at 30° C.)

On the growth of a colorless to pale yellow color, aerial hyphae of white to pink white [5ba, Shell Pink ] are formed. Soluble pigment is not observed.

(12) Cellulose (synthetic liquid added with pieces of filter paper)

The growth is colorless. White colored aerial hyphae are formed in a small quantity. No soluble pigment is observed.

(13) Gelatin stab culture

On a plain gelatin medium (cultured at 20° C.), the growth is colorless or shows pale yellow color. Neither aerial hyphae nor soluble pigment are formed. On a glucosepeptone-gelatin medium (cultured at 27° C.), the growth is of a pale yellow color, and neither aerial hyphae nor soluble pigment are observed.

(14) Skimmed milk (cultured at 37° C.)

The growth is of a pale yellow to pale yellow brown color. No aerial hyphae are formed. Soluble pigment is produced with a slightly brown tinge from about the 18th day of the incubation.

3. Physiological properties (1) Temperature range for the growing

Using starch-inorganic salts-agar medium (ISP-Medium 4), tests for incubation of MI215-NF3 strain were conducted at 20° C., 24° C., 27° C., 30° C., 37° C. and 50° C., respectively. can grow at all the tested temperatures except 50° C. It appears that optimal growth temperature is around 30° C.

(2) Liquefaction of gelatin (15% plain gelatin medium, cultured at 20° C.; glucose-peptone-gelatin medium, cultured at 20° C.)

In the plain gelatin medium, liquefaction of gelatin started from about 11th day after the incubation but is rather weak. In the glucose-peptone-gelatin medium, Liquefaction of gelatin is observed from about 5th day after the incubation and the grade of liquefaction is medium to weak.

(3) Hydrolysis of starch (starch-inorganic salts-agar medium, ISP-Medium 4 and starch-agar medium, all cultured at 30° C.)

In all the tested media, the hydrolysis of starch is observed and the grade of hydrolysis is medium.

(4) Coagulation and peptonization of skimmed milk (skimmed milk, cultured at 37° C.)

From about the fifth day of the incubation, skimmed milk can be coagulated and immediately undergoes complete coagulation, followed by starting of the peptonization. The progress of the peptonization is slow. The peptonization was not completed in three weeks of observation.

(5) Formation of melanoid pigments (tryptone-yeast broth, ISP-Medium 1; peptone-yeast-iron-agar medium, ISP-Medium 6; tyrosine-agar medium, ISP-Medium 7; all cultured at 30° C.)

Formation of melanoid pigment is negative on the tryptone-yeast broth and the tyrosine-agar medium but is probably positive on the peptone-yeast-iron-agar medium.

(6) Utilization of carbon sources (Pridham-Gottlieb agar medium, ISP-Medium 9, cultured at 30° C.)

L-arabinose, D-xylose, D-glucose, D-fructose, rhamnose and D-mannitol are utilizable for growth, but sucrose, inositol, raffinose and lactose are not utilizable.

(7) Liquefaction of calcium malate (calcium malate-agar medium, cultured at 30° C.)

Liquefaction of calcium malate is not observed.

(8) Reduction of nitrate (aqueous solution of peptone containing 0.1% of potassium nitrate, ISP-Medium 8, cultured at 30° C.)

The reduction was positive.

(9) Decomposition of cellulose (Synthetic test solution containing pieces of filter paper added, cultured at 30° C.)

The decomposition was negative.

Summarizing the above-mentioned characteristics, MI215-NF3 strain is morphollogically characterized in that aerial hyphae bear spore chains of hooked or spiral shape and each chain of spores contains 7–15 spores. The surface of spore is warty. Neither whirls nor sporangia are observed. In addition, splitting of substrate mycelia is not observed on various culture media, white to gray white or pink to white colored aerial hyphae are formed on a growth of a pale yellow to pale yellow brown to grayish yellow brown in color. Soluble pigment is produced with slight yellowish tinge.

Formation of melanoid pigments is negative on tryptone-yeast broth and tyrosine-agar medium but positive on peptone-yeast-iron-agar medium. The grade of protein-decomposing activity is medium to weak, while the grade of the activity to hydrolyze starch is medium. Further, the reduction of nitrate is positive.

Furthermore, MI215-NF3 strain contains mesodiaminopimelic acid as a component of the cell and contains glucose, galactose, madurose and ribose as the sugar components in the whole cell, and it shows Type IIIB for the principal constituents of the cell wall according to the proposal by Lechevalier et al. described in the "International Journal of Systematic Bacteriology", 20, 435 (1970). On the other hand, its phospholipids are of the PI type (i.e., do not contain phosphatidyl ethanolamine, phosphatidyl xethylethanolamine, phosphatidyl choline and unknown glycosamine-containing phospholipids but contain phosphatidyl inositol and phosphatidyl inositolmannoside). The menaquinone is composed of MK-9(H$_6$), MK-9(H$_8$) and a small amount of MK-9(H$_4$).

In view of the foregoing, MI215-NF3 strain is considered to be an actinomycete strain belonging to the genus Actinomadura. Among the known strains of the genus Actinomadura, microbial species analogous to MI215-NF3 strain have been searched for. *Actinomadura citrea* [Literature 1: "Antibiotiki", 17, 965-970 (1970); and Literature 2: "Systematic & Applied Microbiology", 6, 264-270 (1985)] can be mentioned as the anologous species in view of its shape and menaquinone composition. Thus, MI215-NF3 strain and *Actinomadura citrea* are very close to each other in that they form the spore chains of a hooked or spiral shape, have warty surface of spores and produce soluble pigments of yellow color on various culture media and that the menaquinone compositions of their cells contain MK-9(H$_6$) and MK-9(H$_8$). However, there remain still many aspects that cannot be determined from the literatures. The present inventors are planning to obtain the standard strain of *Actinomadura citrea* and conduct a comparative experiment with it. In account of these matters, MI215-NF3 strain is named "Actinomadura sp. MI215-NF3" at the present time. Incidentally, MI215-NF3 strain was deposited on Nov. 22, 1988 in "Fermentation Research Institute", Agency of Industrial Science and Technology, Ministry of International Trade and Industry, located at Tsukuba-shi, Ibaraki-ken, Japan, and has been stored there under "FERM P-10397". In addition, MI215-NF3 strain has been deposited under "FERM BP-2675" in terms of the Budapest Treaty.

Further, in a third aspect of the present invention, there is also provided an agent for controlling or therapeutically treating fowl coccidiosis, which contains as an active ingredient MI215-NF3 substance of the formula (I) or a salt thereof.

BEST MODES OF WORKING THE INVENTION

In the process according to the second aspect of the present invention, the production of MI215-NF3 substance is carried out by the following procedures.

Thus, the production of MI215-NF3 substance may preferably be conducted by cultivation of an MI215-NF3 substance-producing microorganism in a nutrient culture medium under submerged aerobic conditions at a temperature of 27-30° C. and under agitation. The nutrient medium employable for that purpose may contain an assimilable carbon source such as sugar, starch, glycerin or molasses, and an organic nitrogen source such as corn steep liquor, soybean flour, cotton seed flour, peptone, meat extract or hop cake, as well as an inorganic nitrogen source such as ammonium sulfate, ammonium nitrate or ammonium chloride. If excessive foaming occurs in the course of fermentation, a defoaming agent such as a vegetable oil or silicone may be added to the fermentation medium. If the pH of the medium during the fermentation varies, a buffering agent such as calcium carbonate may be added. To make the aeration of the culture medium in a submerged incubation tank, it is preferable to continuously feed into the culture medium a flow of fresh air at a rate of about ½ to 2 parts by volume per part by volume of the culture medium broth and per minute. Stirring of the medium may be effected using a stirring means well known in the industry of fermentation.

As a seed culture for the production of MI215-NF3 substance, a cultured material obtained by slant-cultivation of MI215-NF3 strain on an agar medium is employed. This cultured material may be used for inoculation to the culture medium either in a flask for shaking incubation or in a tank for preparation of seed culture. As an alternative, a growth product as obtained from such a shaking incubation flask can be inoculated to the seed-culturing tank.

MI215-NF3 strain usually can grow to a maximum in 5 to 7 days of incubation. However, the time required until a microorganism employed reaches the maximum growth varies depending on the fermentating apparatus, aeration rate, stirring speed and so on. In general, the fermentation is continued until sufficient anti-bacterial potency has been imparted to the culturing medium. Time-dependent variations of the potency of MI215-NF3 substance in the culture broth can be determined by the cup plate assay method using *Staphylococcus aureus* Smith as a test microorganism.

In the process of the present invention, MI215-NF3 substance is recovered from the culture as obtained as above. The recovery of MI215-NF3 substance can be achieved suitably by using such measures which are generally employed for the recovery of metabolic products produced by a microorganism. MI215-NF3 substance can be recovered, for example, by employing, either singly or in combination, such a method which makes use of a difference in the solubility between the desired product and an impurity, such a method which utilizes differences in the adsorption affinity to various adsorbents, and such a method in which the desired product is extracted with a water-immiscible solvent, and the like. In principle, it is preferred to recover MI215-NF3 substance by the following method. Thus, the microbial cells are separated from the culture by filtration or centrifugation. From the resultant filtrate of the culture, the MI215-NF3 substance is extracted with a water-immiscible organic solvent such as n-butyl acetate or ethyl acetate. The resulting extract is then washed with water, and the organic solvent is distilled off from the extract to dryness. The resulting dry residue usually contains MI215-NF3 substance in a proportion of about 10%. To increase the purity of a crude MI215-NF3 substance obtained as the dry residue, the dry residue may be subjected to purification by chromatography with a silica gel column so that MI215-NF3 substance of 95% purity or higher can be obtained. MI215-NF3 substance obtained in the manner described above is usually in the form of a salt such as the sodium or potassium salt or a free carboxylic acid. It can be converted into a single salt by a method known per se in the art. For example, the sodium salt of MI215-NF3 substance may be obtained as colorless plate crystals by dissolving the above MI215-NF3 substance in ethyl acetate, washing the resultant organic solution successively with aqueous 1 mole HCl solution and a saturated aqueous sodium carbonate solution, drying the organic solvent phase over anhydrous sodium sulfate, concentrating the dried solution to dryness and then crystallizing the resultant solid from ethyl acetate-hexane.

MI215-NF3 substance in the free carboxylic acid form can be formed by dissolving MI215-NF3 substance (sodium salt), which has been obtained by purifying a crude MI215-NF3 substance as described just above, in an organic solvent such as ethyl acetate or methanol, and then treating the resultant solution with a strongly acidic ion-exchange resin (H$^+$form) added therein. When MI215-NF3 substance in the free acid form is treated in an organic solvent, for example, with a basic alkali metal salt, e.g., an aqueous solution of sodium carbonate or potassium carbonate or with a basic water-soluble alkaline earth metal compound, e.g., calcium hydroxide or magnesium hydroxide, MI215-NF3 substance in the form of the corresponding alkali metal salt or alkaline earth metal salt can be produced. Similarly, it can also be treated with another metal salt, for example, aluminum hydroxide or ferric hydroxide to prepare the aluminum or iron salt, correspondingly.

In accordance with the third aspect of this invention, the agent for controlling chicken coccidiosis contains MI215-NF3 substance of the formula (I) or a salt thereof as an active ingredient. In this agent, MI215-NF3 substance or its salt as the active ingredient compound may be mixed with a veterinarilly acceptable excipient, for example, starch, cellulose powder, wood-meal or ethanol or with a feed material, similarly to the known drugs for similar applications. The amount of MI215-NF3 substance or its salt in a composition which is prepared by mixing MI215-NF3 substance with such an excipient may be at a concentration of 50–100 ppm which is effective for the therapeutic treatment of coccidiosis. The agent of the present invention for controlling the coccidiosis may also be in the form of a solution of MI215-NF3 substance or its salt in a suitable organic solvent or may be in the form of a concentrate or dispersion of MI215-NF3 substance or its salt suspended in a water-containing organic solvent. Upon use, such a solution or suspension may be added to a feed so that the concentration of the active ingredient substance is in a range from 50 ppm to 100 ppm in the feed.

In a further aspect of the present invention, there is also provided Actinomadura sp. MI215-NF3 strain which is a useful novel microorganism capable of producing the useful antibiotic substance of the formula (I) as described above.

The present invention will hereinafter be illustrated in more detail with reference to Examples.

EXAMPLE 1

Cells of a slant culture of Actinomadura sp. MI215-NF3 strain (FERM BP-2675) were inoculated to a rotary flask of 500-ml capacity containing 110 ml of a seed culture medium which comprised 2% galactose, 2% dextrin for chemical use, 1% soy peptone, 0.5% corn steep liquor, 0.2% ammonium sulfate and 0.2% calcium carbonate and had pH 7.4. The incubation was made at 30° C. for 144 hours on a rotating shaker. The culture broth thus obtained was inoculated at a rate of 3 wt.% to 500-ml rotary flasks each containing 110 ml-aliquoat of a primary culture medium, which comprised 1.5% glycerin, 1.5% soluble starch, 0.5% soybean flour, 1.5% fish meal and 0.2% calcium carbonate and had pH 7.4, with the total volume of the primary culture medium being 5 litres. Each of the thus-inoculated culture media was incubated at 27° C. for 144 hours on a rotating shaker at 180 rpm. The microbial cells were separated by filtration from the culture thus obtained. About 4 l of the resulting culture broth filtrate were extracted with 3 l of ethyl acetate, and the resulting extract was washed with water and then dried over anhydrous sodium sulfate. The dried ethyl acetate solution was filtered to remove insoluble matters, and the filtrate was evaporated to dryness. The residue was dissolved in 100 ml of ethyl acetate. Insoluble matters were again filtered off, and the filtrate was evaporated to dryness so that 2.4 g of a crude product of MI215-NF3 substance were obtained.

EXAMPLE 2

In chloroform were dissolved 2.4 g of the crude product of MI215-NF3 substance as obtained in Example 1. The resulting solution was subjected to chromatography in a column of 150 g of "Xerogel 60" (trade name), a silica gel produced by Merck & Co., Inc., packed with aid of chloroform. The silica gel column was then eluted using chloroform-acetone (5:1) as a developer solvent. MI215-NF3 substance was eluted out in 1600 ml to 3700 ml fractions of the eluate. After the solvent was distilled off from the active fractions under reduced pressure, the residue was dissolved in 90 ml of ethyl acetate. The resultant solution was successively washed with aqueous 0.1 M HCl solution, aqueous 0.1 M sodium hydroxide solution and saturated saline, followed by drying over anhydrous sodium sulfate. The dried solution was thereafter distilled under reduced pressure to remove the solvent, whereby 255 mg of an oily substance was obtained. The oil obtained was crystallized from a mixed solvent of hexane-ethyl acetate so that the sodium salt of MI215-NF3 substance was afforded as colorless plate crystals in a yield of 232 mg.

EXAMPLE 3

In 100 ml of chloroform were dissolved 200 mg of the sodium salt of MI215-NF3 substance. The solution was added with 10 ml of water and then adjusted to pH 3.0 with hydrochloric acid. The resulting mixture was subjected to shaking extraction so that a chloroform layer was obtained- After the chloroform layer as separated was washed with water, it was dried over anhydrous sodium sulfate and then concentrated to dryness. MI215-NF3 substance in the free carboxylic acid form was obtained in a yield of 196 mg.

EXAMPLE 4

MI215-NF3 substance (20 mg) was dissolved in 1 ml of acetone, to which 0.3 ml of a suspension of 2.5% of aluminum hydroxide was added. After reaction at room temperature for 18 hours, 100 ml of water were added to the reaction solution, and the resultant mixture was extracted twice with 100 ml of chloroform. The chloroform layer was washed with water, dried and then concentrated to dryness, to give 19.8 mg of the aluminum salt of MI215-NF3 substance.

INDUSTRIAL UTILIZABILITY OF THE INVENTION

As has been described above, the novel antibiotic, MI215-NF3 substance, or a salt thereof can be obtained by culturing Actinomadura sp. MI215-NF3 strain which has the capability to produce the antibiotic MI215-NF3 substance, and then isolating it from the culture. MI215-NF3 substance and its salts have activities to control or therapeutically treat chicken coccidiosis and also useful antibacterial activities against certain species of bacteria. No particular limitation is imposed on the species of fowls whose infected coccidiosis can be treated by MI215-NF3 substance and its salts according to the present invention. In addition, the antibiotic MI215-NF3 substance and its salts according to the present invention are more effective as compared with conventional anticoccidial antibiotics such as monensin and salinomycin even at a smaller dosage.

The present invention can therefore provide an antibiotic, MI215-NF3 substance and salts thereof which are useful as drugs for animals and as a medicine for men.

We claim:

1. An antibiotic, MI215-NF3 substance, having the following formula (I):

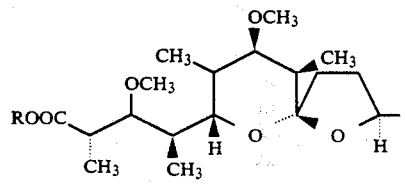 (I)

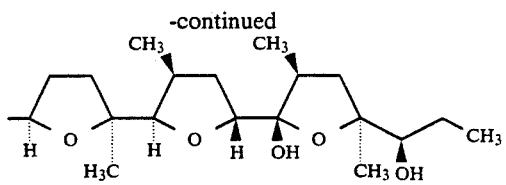

wherein R is a hydrogen atom; and a salt of MI215-NF3 substance of the formula (I) where R is a metal selected from the group, alkaline metal, alkaline earth metal, iron, aluminum and ammonium ion.

2. A composition for controlling chicken coccidiosis, comprising as an active ingredient MI215-NF3 substance having the formula (I) defined in claim 1, or a salt thereof as defined in claim 1 and a carrier therefor.

* * * * *